US012290644B2

(12) United States Patent
Tobin et al.

(10) Patent No.: US 12,290,644 B2
(45) Date of Patent: May 6, 2025

(54) CATHETER PLACEMENT SYSTEM WITH STIFFENING SYSTEM

(71) Applicant: Bard Access Systems, Inc., Salt Lake City, UT (US)

(72) Inventors: Taylor C. Tobin, Nashua, NH (US); Jacquelyn N. Phelps, Cambridge, MA (US); Glade H. Howell, Draper, UT (US); Kyle G. Thornley, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 381 days.

(21) Appl. No.: 17/513,789

(22) Filed: Oct. 28, 2021

(65) Prior Publication Data
US 2022/0126064 A1    Apr. 28, 2022

Related U.S. Application Data

(60) Provisional application No. 63/106,792, filed on Oct. 28, 2020.

(51) Int. Cl.
*A61M 25/09*      (2006.01)
*A61M 25/01*      (2006.01)
*A61M 25/06*      (2006.01)

(52) U.S. Cl.
CPC .... *A61M 25/0102* (2013.01); *A61M 25/0631* (2013.01); *A61M 25/09* (2013.01)

(58) Field of Classification Search
CPC .......... A61M 25/0026; A61M 25/0102; A61M 25/0631; A61M 25/0113; A61M 25/0606; A61M 25/0693
See application file for complete search history.

(56) References Cited

U.S. PATENT DOCUMENTS 1,013,691 A    1/1912   Shields
3,225,762 A    12/1965   Guttman
(Continued)

FOREIGN PATENT DOCUMENTS

DE    202012006191 U1    7/2012
EP        0653220 A1    5/1995
(Continued)

OTHER PUBLICATIONS

U.S. Appl. No. 16/398,020, filed Apr. 29, 2019 Board Decision dated Oct. 30, 2023.
(Continued)

*Primary Examiner* — Nathan R Price
*Assistant Examiner* — Haden Matthew Ritchie
(74) *Attorney, Agent, or Firm* — Rutan & Tucker LLP

(57) ABSTRACT

Disclosed herein is a catheter placement system with a stiffening system and associated methods thereof. The catheter placement system can include a needle, catheter (e.g. rapid insertion central catheter), one or more guidewires, and a stiffening system, configured to place the catheter while containing portions of the catheter placement system that contact the patient within a sterile environment. Advantageously, the catheter placement system can provide all tools necessary for accessing a vasculature, dilating the insertion site and placing the catheter within a single device, mitigating repeated insertion of multiple tools and reducing the risk of introducing pathogens or the like. Further, the overall time required to place the catheter is reduced, reducing patient down time and improving patient outcomes.

11 Claims, 13 Drawing Sheets

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 4,205,675 A | 6/1980 | Vaillancourt |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,935,008 A * | 6/1990 | Lewis, Jr. .......... A61M 25/065 604/510 |
| 4,950,252 A | 8/1990 | Luther et al. |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,158,544 A | 10/1992 | Weinstein |
| 5,188,593 A | 2/1993 | Martin |
| 5,195,962 A | 3/1993 | Martin et al. |
| 5,207,650 A | 5/1993 | Martin |
| RE34,416 E | 10/1993 | Lemieux |
| 5,267,958 A | 12/1993 | Buchbinder et al. |
| 5,295,970 A | 3/1994 | Clinton et al. |
| 5,306,247 A | 4/1994 | Pfenninger |
| 5,312,361 A | 5/1994 | Zadini et al. |
| 5,322,512 A | 6/1994 | Mohiuddin |
| 5,328,472 A | 7/1994 | Steinke et al. |
| 5,350,358 A | 9/1994 | Martin |
| 5,358,495 A | 10/1994 | Lynn |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,460,185 A | 10/1995 | Johnson et al. |
| 5,489,271 A | 2/1996 | Andersen |
| 5,573,520 A | 11/1996 | Schwartz et al. |
| 5,683,370 A | 11/1997 | Luther et al. |
| 5,713,876 A | 2/1998 | Bogert et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,921,971 A | 7/1999 | Agro et al. |
| 5,947,940 A | 9/1999 | Beisel |
| 5,957,893 A | 9/1999 | Luther et al. |
| 5,971,957 A | 10/1999 | Luther et al. |
| 6,159,198 A | 12/2000 | Gardeski et al. |
| 6,206,849 B1 | 3/2001 | Martin et al. |
| 6,228,062 B1 | 5/2001 | Howell et al. |
| 6,475,187 B1 | 11/2002 | Gerberding |
| 6,551,284 B1 | 4/2003 | Greenberg et al. |
| 6,606,515 B1 | 8/2003 | Windheuser et al. |
| 6,616,630 B1 | 9/2003 | Woehr et al. |
| 6,626,869 B1 | 9/2003 | Bint |
| 6,638,252 B2 | 10/2003 | Moulton et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,094,222 B1 | 8/2006 | Siekas et al. |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,361,011 B2 | 1/2013 | Mendels |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,067,023 B2 | 6/2015 | Bertocci |
| 9,126,012 B2 | 9/2015 | McKinnon et al. |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 * | 3/2018 | Tal .................... A61M 25/0102 |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |

(56) References Cited

U.S. PATENT DOCUMENTS

| | | |
|---|---|---|
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,688,281 B2 | 6/2020 | Blanchard et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,400,260 B2 | 8/2022 | Huang et al. |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1* | 9/2009 | Tal .................... A61M 25/0618 604/103.06 |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0190778 A1* | 8/2011 | Arpasi .............. A61M 25/0026 606/108 |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1* | 8/2015 | Blanchard ......... A61M 25/0618 604/164.08 |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1* | 8/2016 | Mitchell ........... A61M 25/0029 |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0331938 A1 | 11/2016 | Blanchard et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |

(56) References Cited

U.S. PATENT DOCUMENTS

| | | | |
|---|---|---|---|
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1 | 11/2019 | Ribelin et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1* | 4/2021 | DiCianni ........ A61M 25/09041 |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1* | 8/2021 | Kujawa ............ A61M 25/0075 |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0062596 A1 | 3/2022 | Ribelin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331562 A1 | 10/2022 | Jaros et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1 | 6/2023 | Parikh et al. |
| 2023/0233814 A1 | 7/2023 | Howell et al. |
| 2023/0381459 A1 | 11/2023 | Belson et al. |
| 2024/0009427 A1 | 1/2024 | Howell et al. |
| 2024/0050706 A1 | 2/2024 | Howell et al. |
| 2024/0198058 A1 | 6/2024 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 9857685 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A1 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016178974 A1 | 11/2016 |
| WO | 2016187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |

(56) References Cited

FOREIGN PATENT DOCUMENTS

| | | | |
|---|---|---|---|
| WO | 2020/113123 | A1 | 6/2020 |
| WO | 2021038041 | A1 | 3/2021 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2021226050 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/237,909, filed Apr. 22, 2021 Notice of Allowance dated Oct. 27, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Final Office Action dated Jul. 27, 2023.
U.S. Appl. No. 17/392,061, filed Aug. 2, 2021 Final Office Action dated Nov. 21, 2023.
U.S. Appl. No. 17/557,924, filed Dec. 21, 2021 Non-Final Office Action dated Nov. 3, 2023.
PCT/US2020/052536 filed Sep. 24, 2020 International Search Report and Written Opinion dated Dec. 4, 2020.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064642 filed Dec. 21, 2021 International Search Report and Written Opinion dated May 11, 2022.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/240,591, filed Apr. 26, 2021 Final Office Action dated Dec. 6, 2023.
U.S. Appl. No. 17/358,504, filed Jun. 25, 2021 Final Office Action dated Mar. 13, 2024.
U.S. Appl. No. 17/360,694, filed Jun. 28, 2021 Non-Final Office Action dated Feb. 14, 2024.

(56) References Cited

OTHER PUBLICATIONS

U.S. Appl. No. 17/390,682, filed Jul. 30, 2021 Non-Final Office Action dated Dec. 1, 2023.
U.S. Appl. No. 17/392,061, filed Aug. 2, 2021 Advisory Action dated Feb. 14, 2024.
U.S. Appl. No. 17/557,924, filed Dec. 21, 2021 Final Office Action dated Feb. 29, 2024.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/358,504, filed Jun. 25, 2021 Notice of Allowance dated Jul. 17, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Non-Final Office Action dated Jun. 4, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Non-Final Office Action dated Apr. 23, 2024.
U.S. Appl. No. 17/554,978, filed Dec. 17, 2021 Non-Final Office Action dated Apr. 19, 2024.

* cited by examiner

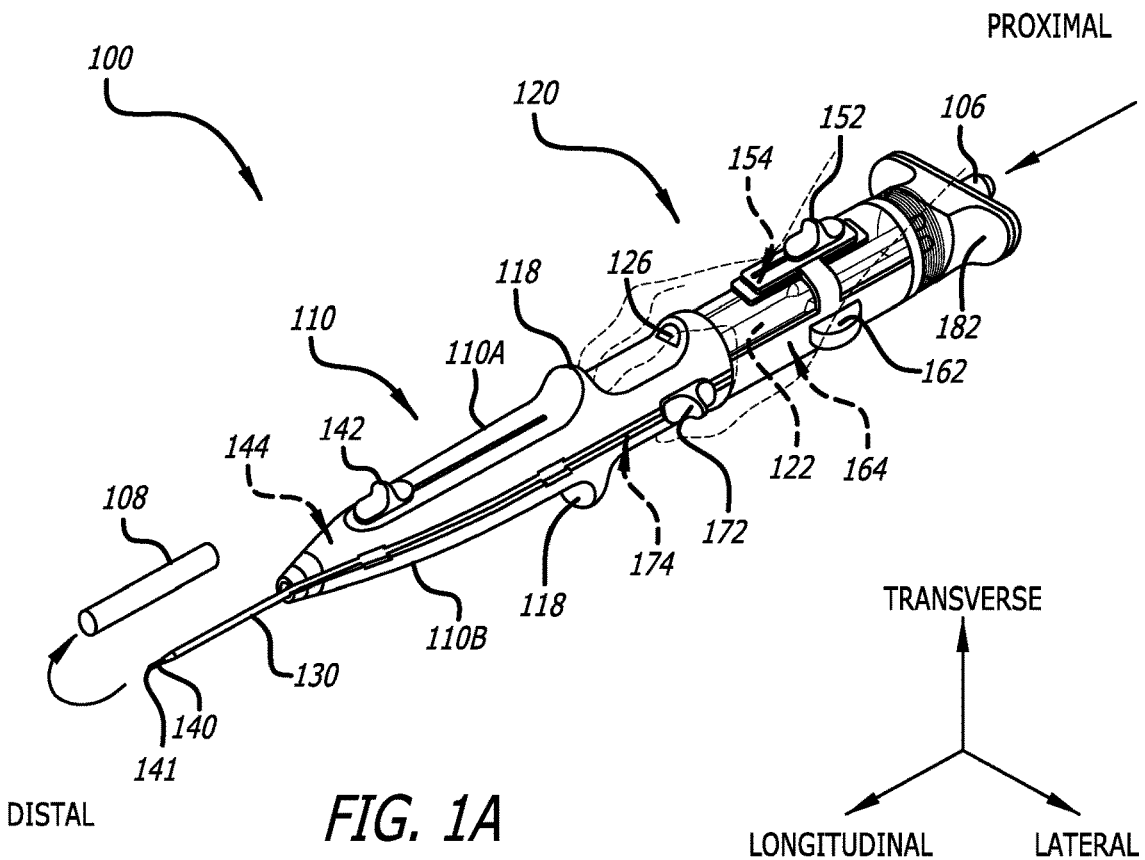
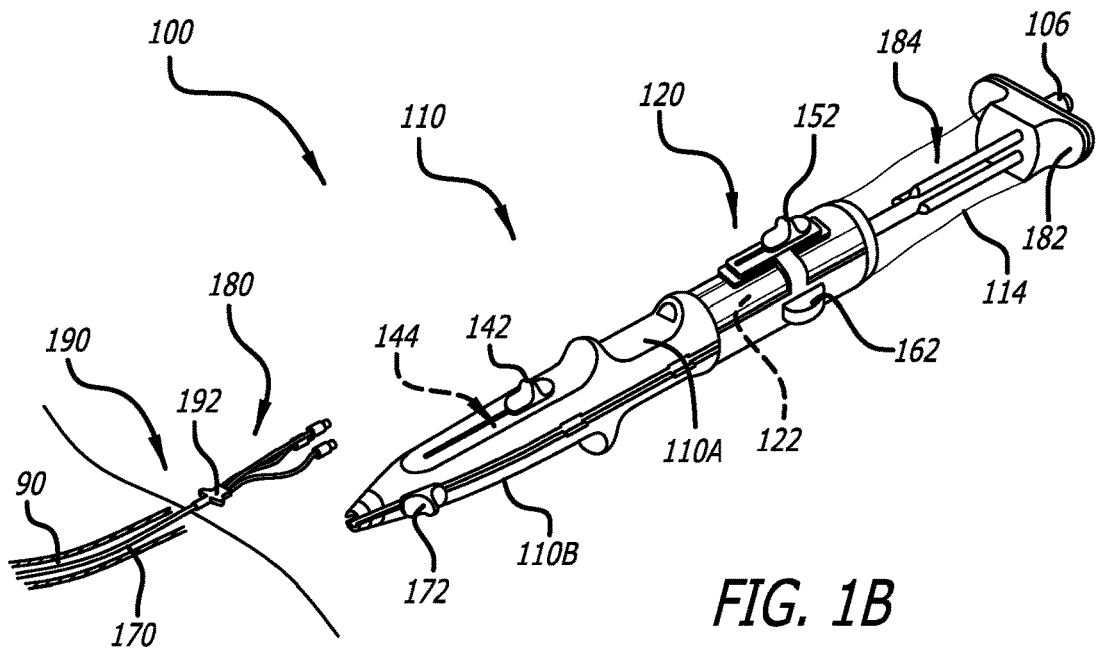

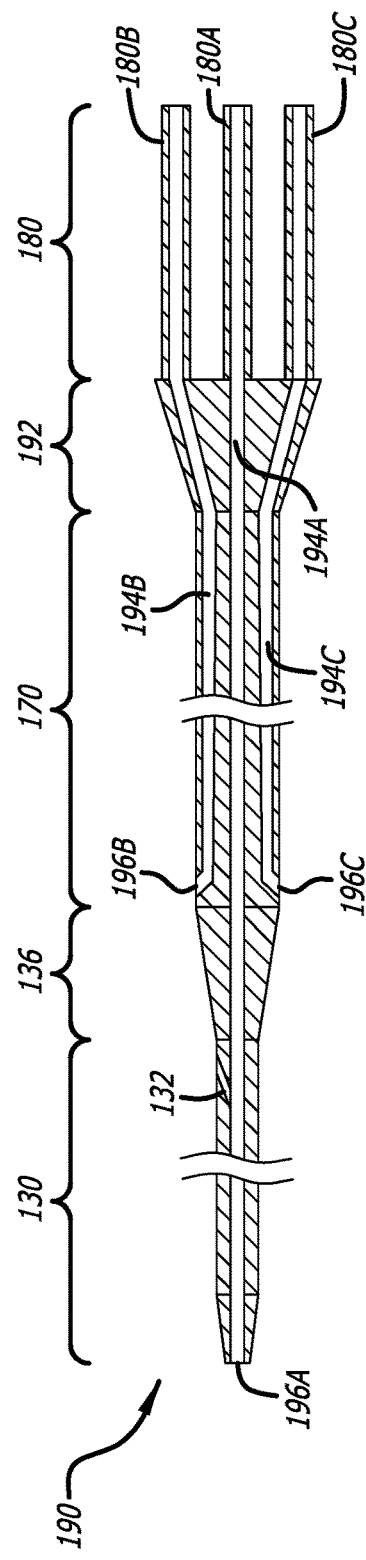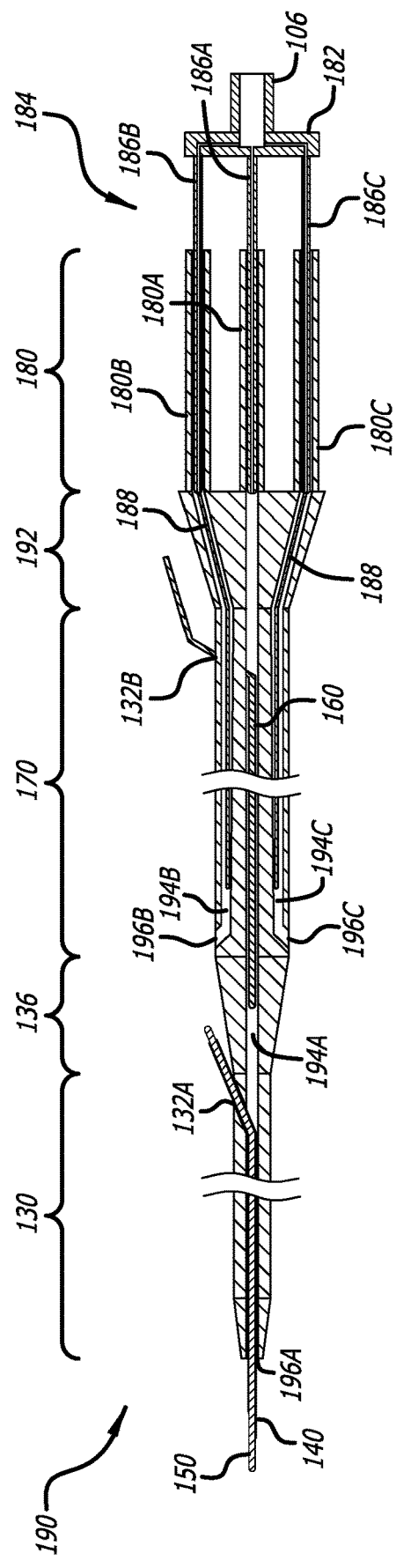
FIG. 2A
FIG. 2B

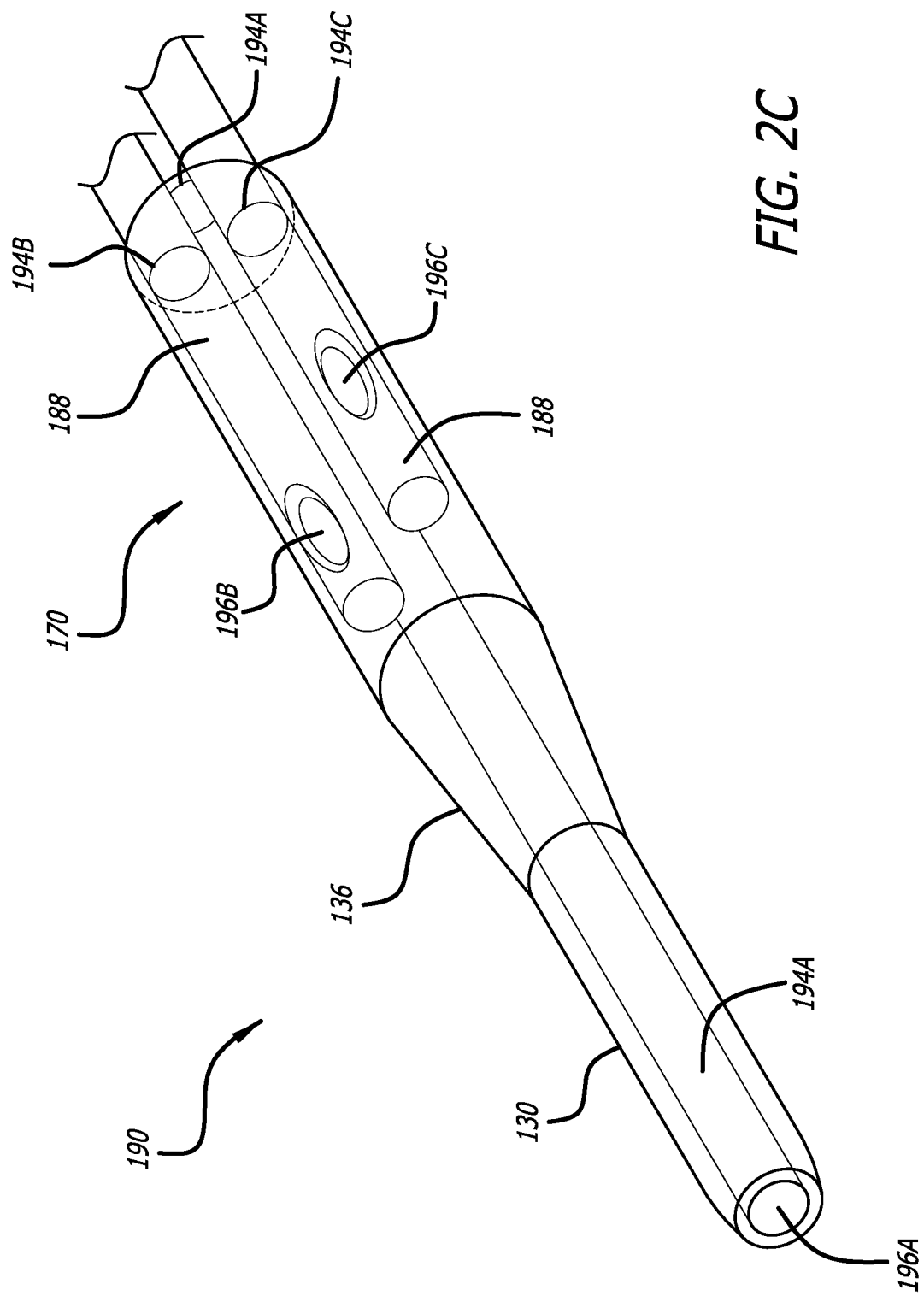

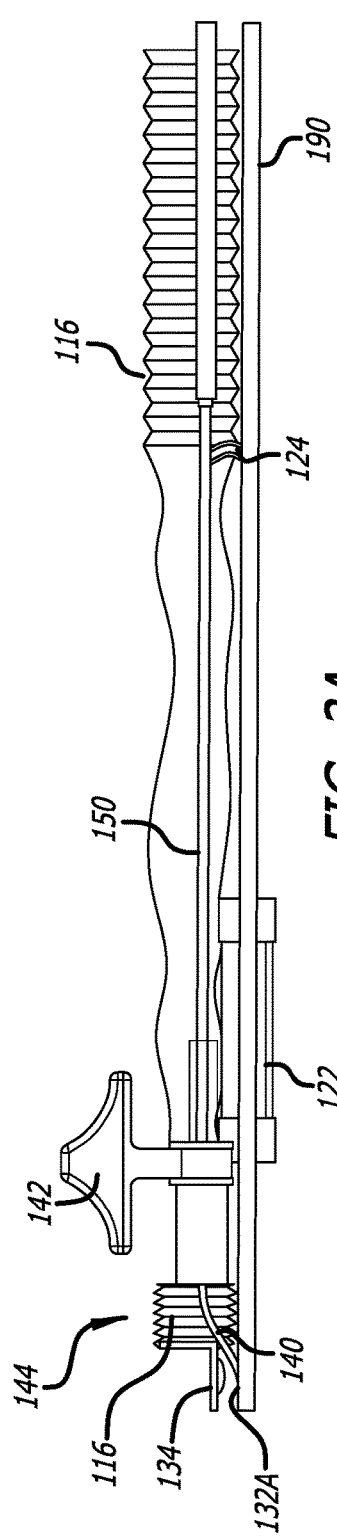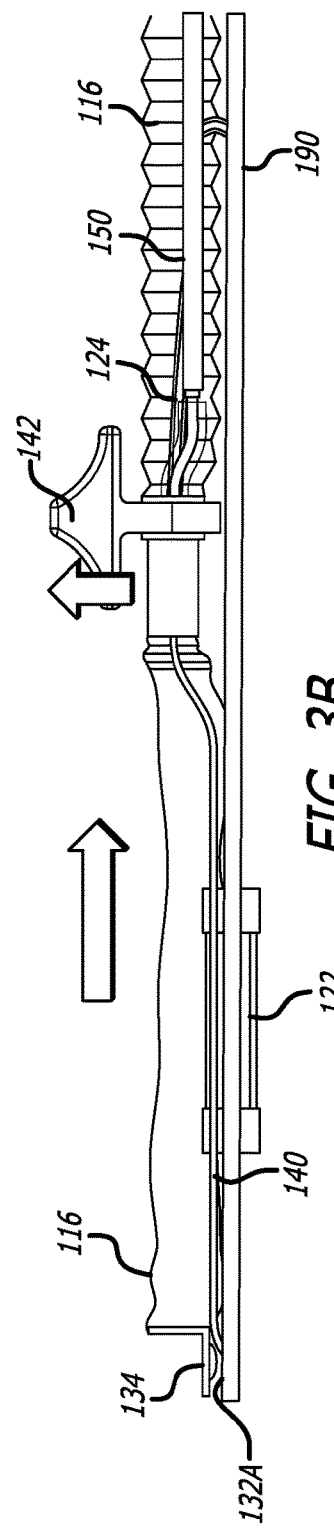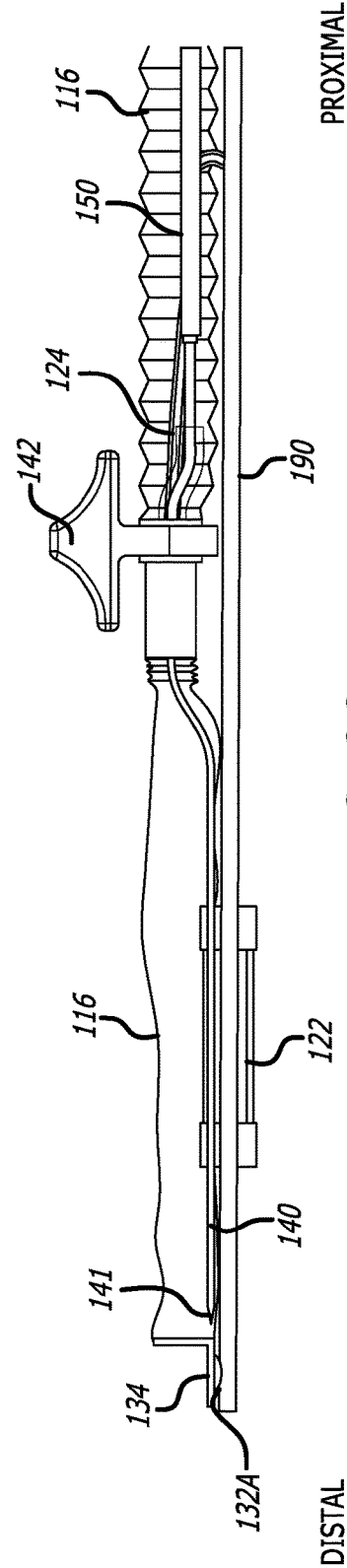

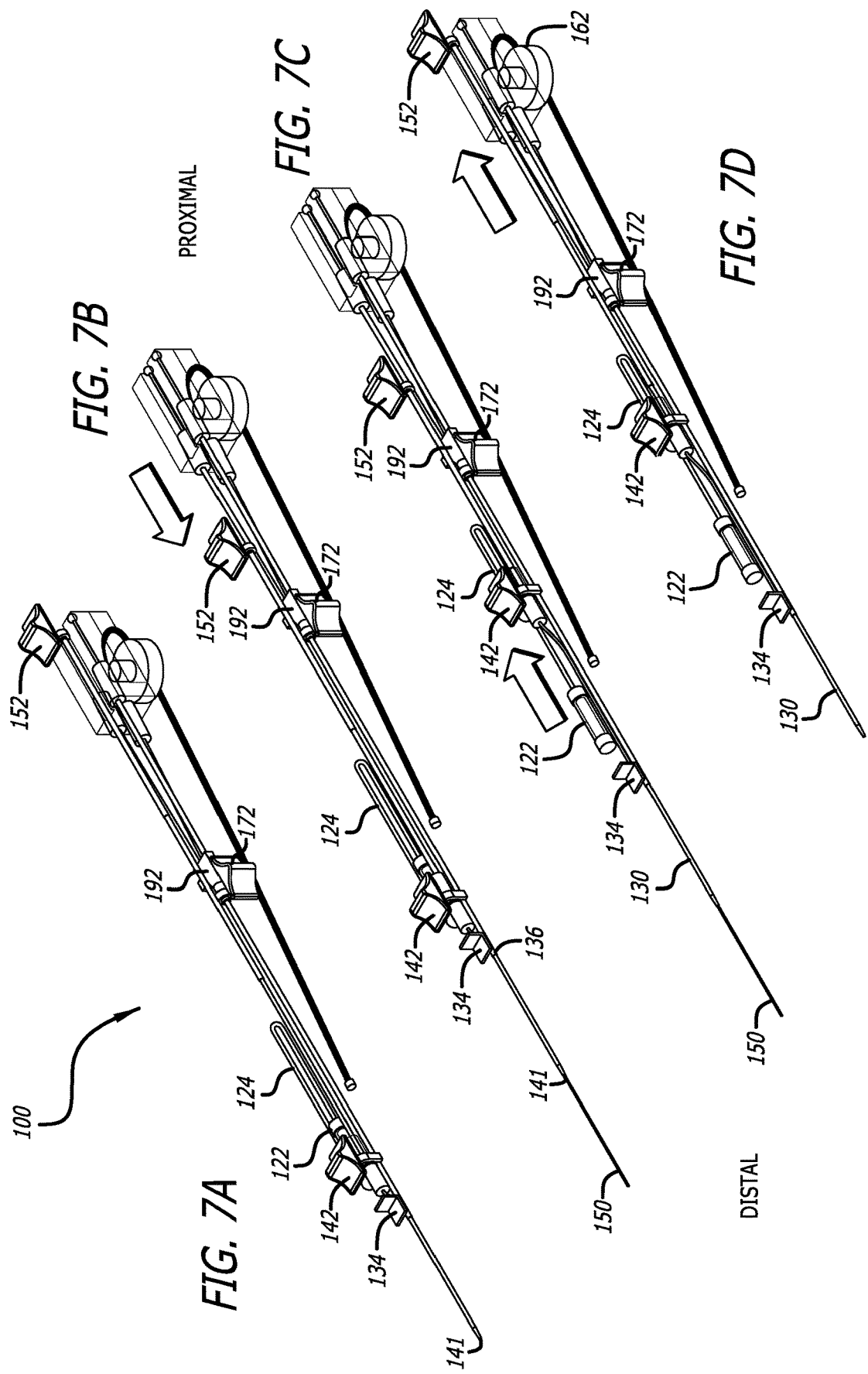

CATHETER PLACEMENT SYSTEM WITH STIFFENING SYSTEM

PRIORITY

This application claims the benefit of priority to U.S. Provisional Application No. 63/106,792, filed Oct. 28, 2020, which is incorporated by reference in its entirety into this application.

SUMMARY

Embodiments disclosed herein are directed to a catheter placement system with a stiffening system and associated methods thereof. The catheter placement system can include a needle, catheter (e.g. rapid insertion central catheter), one or more guidewires, and a stiffening system, configured to place the catheter while containing portions of the catheter placement system that contact the patient within a sterile environment. Advantageously, the catheter placement system can provide all tools necessary for accessing a vasculature, dilating the insertion site and placing the catheter within a single device, mitigating repeated insertion of multiple tools and reducing the risk of introducing pathogens, or the like. Further, the overall time required to place the catheter is reduced, reducing patient down-time and improving patient outcomes. Advantageously, the stiffening system can support the catheter, or portions thereof disposed outside of the patient. The stiffening system can remain outside of the body as the catheter is placed and allow for more rigid materials to support the catheter.

Disclosed herein is catheter placement system including, a housing defining an interior cavity and configured to maintain a sterile environment therein, a catheter defining a first lumen and including a first section, a second section, and a transition section disposed therebetween, one or both of the transition section and the second section disposed within the sterile environment defined by the housing, and a stiffening system including a first stylet defining a stylet lumen and extending proximally into a proximal portion of the first lumen.

In some embodiments, the catheter placement system further includes a needle extending through a first side port of the catheter into a distal portion of the first lumen, a distal portion of the needle and a distal portion of the first section extending from a distal end of the housing. In some embodiments, the catheter placement system further includes a needle retraction assembly configured to withdraw the needle proximally from the first lumen and dispose the needle in an offset position from an axis of the first lumen within the interior cavity.

In some embodiments, the catheter placement system further includes a first guidewire advancement assembly configured to advance a first guidewire through the first side port of the catheter and through a distal portion of the first lumen. In some embodiments, the catheter placement system further includes a second guidewire assembly including a scroll wheel actuator configured to rotate and advance a second guidewire through the first lumen. In some embodiments, the stiffening system includes a second stylet extending proximally into a proximal portion of a second lumen of the catheter, the second stylet including a stylet guidewire extending distally therefrom into the second section of the catheter.

In some embodiments, the second lumen communicates with a distal opening disposed in a sidewall of the second section, a distal portion of the stylet guidewire configured to selectively occlude the distal opening. In some embodiments, the catheter placement system further includes a catheter advancement assembly configured to advance the catheter distally, and configured to separate a top half of the housing from a bottom half of the housing when advanced to a distal position. In some embodiments, the catheter placement system further includes a manifold including a flushing hub in fluid communication with the stylet lumen, the manifold configured to support the stiffening system. In some embodiments, the catheter placement system further includes a blood flash indicator disposed within the interior cavity and in fluid communication with a lumen of the needle.

Also disclosed is a method of placing a catheter including, providing a catheter placement system having a housing defining a sterile environment and including a needle, a catheter defining a first catheter lumen, and a stiffening system including a stylet having a stylet lumen and in fluid communication with the first catheter lumen, flushing the first catheter lumen by providing a fluid through the stylet lumen, accessing a vasculature of a patient by creating an insertion site with the needle, advancing a first section of the catheter through the insertion site, withdrawing the needle from a lumen of the first section, dilating the insertion site by advancing a transition section of the catheter through the insertion site, advancing a second section of the catheter into the vasculature, and withdrawing the stiffening system from the first catheter lumen.

In some embodiments, the catheter includes the first section disposed at a distal end, the transition section extending proximally from the first section, a second section extending proximally from the transition section, a hub disposed at a proximal end of the second section and an extension set extending proximally from the hub, the extension set including a first extension leg in fluid communication with the first catheter lumen. In some embodiments, the method further includes advancing one of a first guidewire or a second guidewire through a portion of the first lumen into a vasculature of a patient. In some embodiments, advancing the second section of the catheter into the vasculature further includes separating a top half of the housing from a bottom half of the housing.

In some embodiments, the method further includes disengaging the catheter from the catheter placement system by urging the catheter between the top half of the housing and the bottom half of the housing. In some embodiments, the method further includes a manifold having a flushing hub and configured to provide fluid communication between the flushing hub and the stylet lumen. In some embodiments, the method further includes sliding the manifold proximally relative to the housing to withdraw the stiffening system from the first catheter lumen.

In some embodiments, the method further includes actuating a blood flash actuator to provide fluid communication between a lumen of the needle and an interior cavity of a blood flash indicator. In some embodiments, a vacuum is disposed within the interior cavity of the blood flash indicator to draw a fluid flow proximally through the needle lumen.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1B illustrate perspective views of a catheter placement system, in accordance with embodiments disclosed herein.

FIGS. 2A-2B illustrate cross-section schematic views of a catheter, in accordance with embodiments disclosed herein.

FIG. 2C illustrates a close up view of a distal portion of a catheter, in accordance with embodiments disclosed herein.

FIGS. 3A-3C illustrate side views of a needle insertion assembly, in accordance with embodiments disclosed herein.

FIGS. 7A-7D illustrate steps in an exemplary method of use of a catheter placement system with the outer housings removed for ease of illustration, in accordance with embodiments disclosed herein.

DESCRIPTION

Figure 1C:
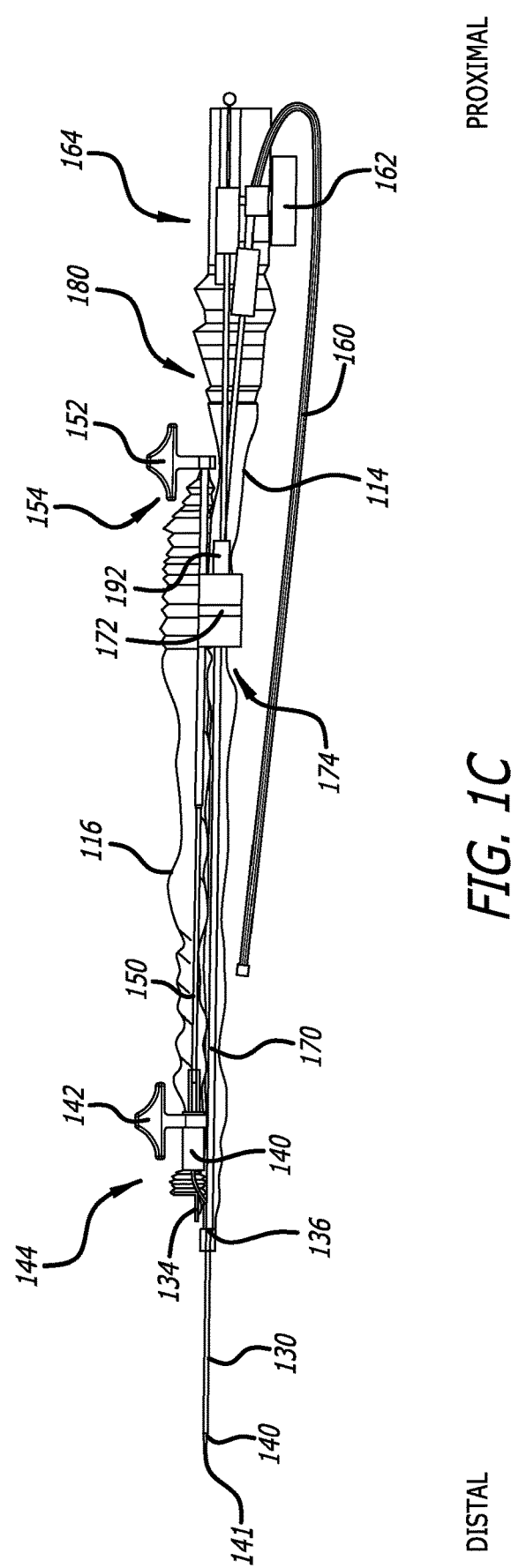
FIG. 1C illustrates a side view of the catheter placement system of FIG. 1A with the outer housings removed for ease of illustration, in accordance with embodiments disclosed herein.
Figure 4A:
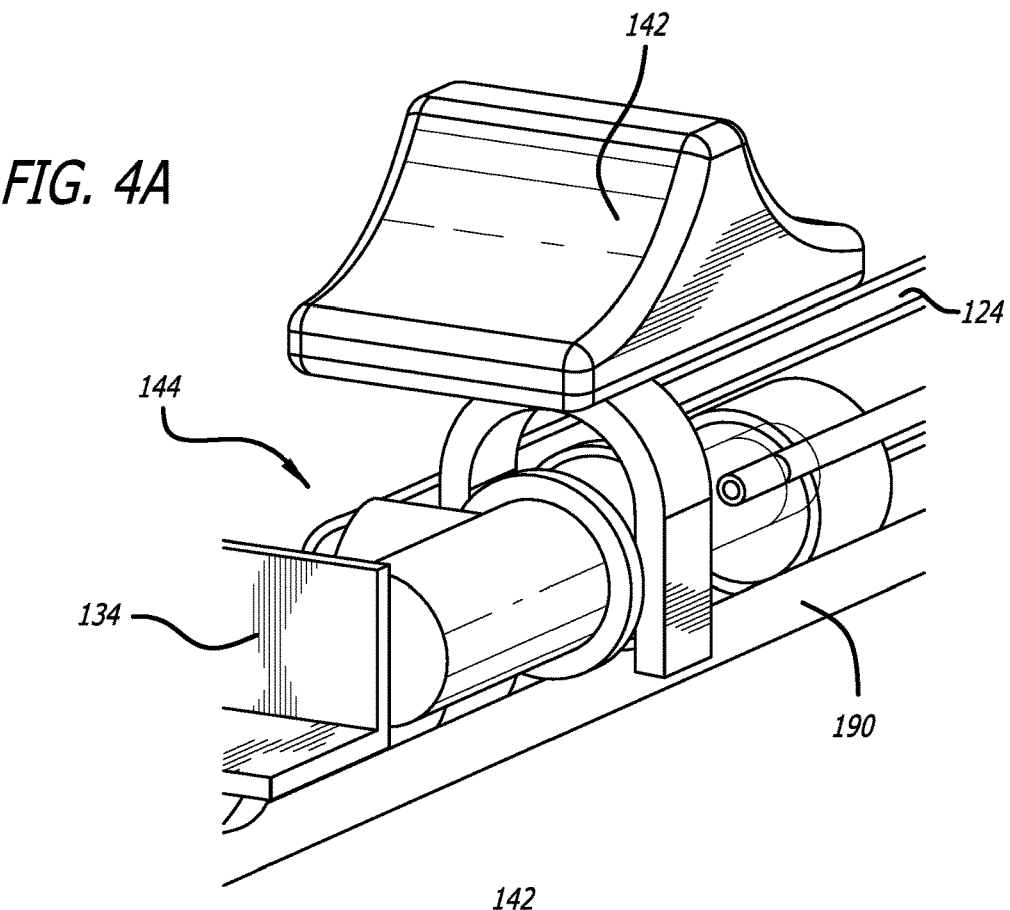
FIGS. 4A-4B illustrate perspective views of a needle insertion assembly, in accordance with embodiments disclosed herein.
Figure 4B:
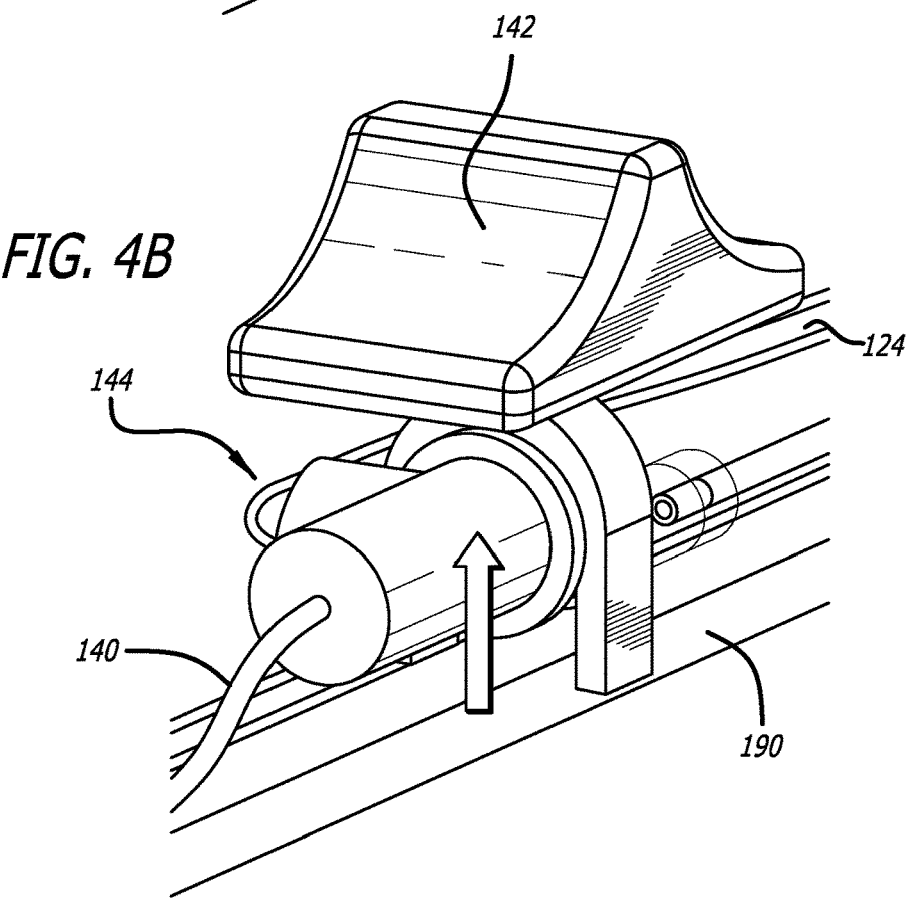

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

As shown in FIG. 1A, and to assist in the description of embodiments described herein, a longitudinal axis extends substantially parallel to an axial length of a needle 140. A lateral axis extends normal to the longitudinal axis, and a transverse axis extends normal to both the longitudinal and lateral axes. A horizontal plane is defined by the longitudinal and lateral axes, a vertical plane extends normal thereto.

Unless defined otherwise, all technical and scientific terms used herein have the same meaning as commonly understood by those of ordinary skill in the art.

The present disclosure generally relates to a catheter placement system ("system") 100 including a stiffening system, and associated methods thereof. In an embodiment, the catheter placement system 100 can be used to place a catheter, such as for example, a Rapid Insertion Central Catheter ("RICC") 190 to access a vasculature of a patient. However, it will be appreciated that embodiments disclosed herein can be used to place various catheters, cannulas, single lumen catheters, multi-lumen catheters, intravenous (IV) catheters, peripheral intravenous line (PIV) catheters, peripherally inserted central catheters (PICC), central venous catheter (CVC), dialysis catheters, drainage catheters, and the like, without limitation.

FIGS. 1A-1C show an exemplary embodiment of a catheter placement system ("system") 100. FIG. 1A shows a perspective view of the system 100 prior to deployment of a catheter, e.g. a catheter 190. FIG. 1B shows a perspective view of the system 100 after the catheter 190 has been placed. FIG. 1C shows a side view of the interior components of the system 100 with the exterior housings 110, 120 removed for ease of explanation.

The system 100 generally includes one or more exterior housings, such as a splittable catheter housing ("catheter housing") 110 and a guidewire housing 120, coupled to a proximal end thereof. The system 100 further includes a needle 140, a catheter 190 such as a Rapid Insertion Central Catheter (RICC), an extension set 180, one or more guidewires 150, 160, and a stiffening system 184, portions of which can be disposed within an interior cavity defined by the one or more exterior housings 110, 120.

In an embodiment, the catheter 190 can include one or more sections configured to display different mechanical properties. For example, the catheter 190 can include a first section 130 disposed at a distally, a second section 170 disposed proximally. The catheter 190 can further include a transition section 136 disposed therebetween, as described in more detail herein. Further, the system 100 can include a first guidewire 150 and a second guidewire 160, as described in more detail herein.

The catheter housing 110 and the guidewire housing 120 can co-operate to define an elongate, cylindrical shape including a tapered distal portion and a substantially circular cross-sectional shape. However, it will be appreciated that other elongate profiles and cross-sectional shapes including triangular, square, hexagonal, polygonal, or combinations thereof, are also contemplated. In an embodiment, a portion of the catheter housing 110 and/or the guidewire housing 120 can define a faceted surface to provide a gripping surface and facilitate manipulation of the system 100. In an embodiment, the catheter housing 110 and/or the guidewire housing 120 can include a protrusion 118 configured to provide an abutment surface for a user to facilitate manipulation of the system 100. In an embodiment, the catheter housing 110 and/or the guidewire housing 120 can be formed of a rigid or semi-rigid material including metal, alloy, polymer, plastic, thermoplastic, elastomer, rubber, silicone rubber, composite, combinations thereof, or the like.

In an embodiment, an outer surface of the catheter housing 110 or the guidewire housing 120 includes a compliant material, elastomer, silicone rubber, or the like, with an increased friction co-efficient, to provide a comfortable gripping surface and facilitate grasping and manipulation of the system 100. In an embodiment, the catheter housing 110 or the guidewire housing 120, or portion thereof, can be formed of a translucent or transparent material to allow a user to observe structures, components, catheters, guidewires, extension sets, elongate medical devices, or the like, disposed therein. As used herein, an "elongate medical device" can include the catheter 190 or portion thereof such as the first section 130 or the second section 170, the needle 140, the first guidewire 150, the second guidewire 160, one or more advancement assemblies, combinations thereof, or the like.

In an embodiment, the catheter housing 110 can include a top housing piece 110A and a bottom housing piece 110B that are releasably engage along a horizontal plane. The top housing piece 110A and the bottom housing piece 110B are configured to selectively detach and disengage from the catheter 190 once the catheter 190 is placed within the vasculature 90 of the patient. In an embodiment, the housing pieces 110A, 110B can be engaged along a longitudinal vertical plane to provide a left housing piece 110A and a right housing piece 110B, or along a plane angled relative to the horizontal or vertical plane.

In an embodiment, a guidewire housing 120 can extend from a proximal end of the catheter housing 110 and define an interior cavity that communicates with an interior cavity of the catheter housing 110. In an embodiment, the guidewire housing 120, or portion thereof, can be formed of a transparent material to allow a user to observe a portion of the catheter 190, the blood flash indicator 122, or an elongate medical device, or the like, disposed therein.

The system 100 can further include an extension set manifold ("manifold") 182, disposed at a proximal end of the guidewire housing 120 and configured to slide proximally along a longitudinal axis between a distal position (FIG. 1A) and a proximal position (FIG. 1B). The manifold 182 can support a stiffening system 184 that comprises one or more stylets 186 or stylet guidewires 188. The manifold 182 can include one or more tabs, wings, or protrusions configured to provide increased grip for a user to slide the manifold 182 to the proximal position and remove the stiffening system 184 from the catheter 190. The manifold 182 can include a flexible film barrier 114 extending between a distal end of the extension set manifold 182 and a proximal end of the guidewire housing 120 and extend annularly about a longitudinal axis. In an embodiment, the barrier 114 can be formed of a thin polymer film or similar flexible material, and can be configured to collapse to allow the manifold 182 to transition between the distal position and the proximal position. In an embodiment, the barrier 114, or portion thereof, can be transparent to allow a user to observe one or more components, elongate medical devices, or the like, disposed therein.

In an embodiment, the catheter housing 110, guidewire housing 120, and/or one or more barriers, e.g. barriers 114, can define an interior cavity configured to receive one or more elongate medical devices, advancement assemblies, or the like, therein. Advantageously, the interior cavity can maintain the elongate medical devices etc., within a sterile environment, allowing a user to manipulate the system 100 without having to directly contact the elongate medical devices. This maintains the elongate medical device(s) etc. in a sterile environment and mitigates the introduction of pathogens, or similar infection causing agents.

In an embodiment, one or more flexible film barriers can be disposed within the interior cavity of the system 100 to contain one or more elongate medical devices within a sterile environment. For example, as shown in FIG. 1C, a first sterile barrier 114 can contain the extension set 180 and a portion of the catheter 190. A second sterile barrier 116 can contain the first guidewire 150 and the needle 140 in the retracted state. These and other combinations of sterile barriers and elongate medical devices are also contemplated.

As shown in FIG. 1C, the catheter placement system 100 can include a needle retraction assembly 144, a catheter advancement assembly 174, a first guidewire advancement assembly 154, and a second guidewire advancement assembly 164. In an embodiment, the system 100 can include a Rapid Insertion Central Catheter ("RICC") 190. The catheter 190 can be disposed within the interior cavity formed by the catheter housing 110 and the guidewire housing 120. The catheter 190 can be coupled with the catheter advancement assembly 174 and both the catheter 190 and the catheter advancement assembly 174 can be slidable relative to the catheter housing 110 or the guidewire housing 120, along a longitudinal axis.

The catheter advancement assembly 174 can be coupled with a catheter actuator 172 disposed on an outer surface of the catheter housing 110. Transitioning the catheter actuator 172 between a proximal position (FIG. 1A) and a distal position (FIG. 1B) can transition the catheter advancement assembly 174 and the catheter 190 between the retracted position and the extended position. In use, a user can manipulate the catheter actuator 172 to advance the catheter 190, or similar catheter device, into the vasculature 90.

FIGS. 2A-2B show further details of an exemplary catheter 190. The catheter 190 can include a first section 130 disposed at a distal end of the catheter 190, and a second section 170 disposed proximally. In an embodiment, the catheter 190 can further include a transition section 136 disposed between the first section 130 and the second section 170.

In an embodiment, the catheter 190 can further including a hub 192 disposed at a proximal end of the second section 170. The catheter 190 can further include an extension set 180 extending proximally from the hub 192 and comprising one or more extension legs, each communicating with a lumen of the catheter 190. For example, a first extension leg 180A can communicate with a first lumen 194A, a second extension leg 180B can communicate with a second lumen 194B and a third extension leg 180C can communicate with a third lumen 194C. Each extension leg can include a connector such as a luer lock, or the like, disposed at a proximal end thereof. The connector can be configured to couple the extension leg with a syringe, medical fluid line, or the like, to provide fluid communication with a lumen.

In an embodiment, each lumen 194 can communicate with a distal opening 196. For example, the first lumen 194A can extend from the first extension leg 180A, through the hub 192, the second section 170 and the transition section 136, to a first distal opening 196A, disposed at a distal tip of the first section 130. In an embodiment, one of the second lumen 194B or the third lumen 194C can extend from the second extension leg 180B or the third extension leg 180C, respectively, through the hub 192 to the second section 170 and communicate with a respective second distal opening 196B or a third distal opening 196C, disposed in a side wall of the second section 170. In an embodiment, one of the distal openings 196A, 196B, 196C can be disposed in a transition section 136.

In an embodiment, the catheter 190 can include one or more side entry ports ("side ports") 132, extending through a side wall of one of the first section 130, transition section 136, or second section 170, and communicating with one of the first lumen 194A, second lumen 194B, or third lumen 194C. For example, the first section 130 can include a first side port 132A. A needle 140 or a first guidewire 150 can extend through the first side port 132A, and through a distal portion of the first lumen 194A, through the first distal opening 196A to extend distally of the distal tip of the catheter 190.

In an embodiment, the first section 130 can define a relatively smaller diameter than the second section 170. In an embodiment, the first section 130 can define a relatively more rigid, more resilient, or harder durometer than the second section 170. As such, one or both of the first section 130 and the transition section 136 can provide greater columnar strength relative to the second section 170. In an embodiment, the first section 130 can define a single lumen and define a diameter similar to that of a peripheral intravenous (PIV) catheter. In an embodiment, the second section 170 can define two or more lumen, and define a diameter similar to that of a central venous catheter (CVC). The first section 130 can further include a tapered tip, tapering distally from the diameter of the first section 130 to the diameter of the needle 140, to facilitate insertion of the first section 130 through the access site formed by the needle 140. In an embodiment, the transition section 136 can define a tapered or frusto-conical shape extending from the diameter of the first section 130 to the diameter of the second section 170.

Advantageously, the first section 130 can access a vasculature more easily, due to the relatively smaller diameter. Further, if the incorrect vessel is accessed, removing the first section 130 and closing the access site is more easily achieved due to the smaller size of the access site. If the correct vessel is accessed, the catheter 190 can be urged distally such that the transition section 136 is urged through the access site to dilate the access site from the diameter of the first section 130 to the diameter of the second section 170. The stiffening system 184 can support a portion of the catheter 190, e.g. the second section 170, hub 192, or extension set 180 etc., as the catheter 190 is urged into the vasculature 90. In an embodiment, the catheter 190 or sections thereof can be formed of a plastic, polymer, elastomer, urethane, polyether ether ketone (PEEK), fluorinated ethylene propylene (FEP), or similar suitable material. Advantageously, the stiffening system 184 can be formed of a rigid or resilient material and can support the catheter 190, or sections thereof, which remain outside of the patient as the catheter 190 is advanced into the vasculature. The catheter 190 can be advanced while the stiffening system 184 remains stationary, allowing the stiffening system to support portions of the catheter 190 that remain exterior to the patient. Optionally, the stiffening system 184 can be withdrawn proximally to fully remove the stiffening system 184 from the catheter 190. Since portions of the stiffening system 184, e.g. stylets 186, remain exterior to patient, they can be formed of a more rigid material, and provide greater columnar support to the catheter 190.

FIG. 2B shows an exemplary catheter 190 including a needle 140 and a first guidewire 150 entering the lumen of the first section 130, i.e. a distal portion of the first lumen 194A, by way of a first side port 132A extending through a side wall of the catheter 190. The catheter 190 can further include a second guidewire 160 entering the first lumen 194A of the second section 170 of the catheter 190 by way of a second side port 132B. In an embodiment, the second guidewire 160 can enter the first lumen 194A through the first extension leg 180A. Once the needle 140 and the first guidewire 150 are removed, the second guidewire 160 can be advanced through the first lumen 194A, through the first distal opening 196A into a vasculature 90 to facilitate advancing the second section 170 into the vasculature 90.

The catheter placement system 100 can further include a stiffening system 184 comprising one or more support stylets ("stylets") 186 extending distally from the manifold 182. In an embodiment, a stylet 186 can further include a guidewire 188 extending from the distal end thereof. As described herein, the stylets 186 remain outside of the patient and can be formed of a substantially rigid or resilient material. The stylet guidewires 188 can be formed of a relatively more flexible material, or display more flexible characteristics relative to the stylets 186. As such, the stiffening system 184 can provide additional support or stiffening properties to the catheter 190 during placement. In an embodiment, one of the stylet(s) 186, and optionally the stylet guidewires 188 remain stationary relative to the system 100 as the catheter 190 is advanced distally. As such the stiffening system 184 is passively withdrawn from the catheter 190 as the catheter 190 is placed, leaving at least the stylets 186 and optionally the stylet guidewires 188 exterior to the patient and supporting portions of the catheter 190 that remain exterior to the patient. As such, the stiffening system 184 can display more rigid mechanical properties and can provide increase columnar support during placement. During placement, or after the catheter 190 has being placed, the stiffening system 184 can be removed proximally.

In an embodiment, the stiffening system 184 can include a first stylet 186A extending distally into the lumen of the first extension leg 180A, i.e. a proximal portion of the first lumen 194A, a second stylet 186B extending distally into the lumen of the second extension leg 180B, and a third stylet 186C extending distally into the lumen of the third extension leg 180C. Further, in an embodiment, one of the second stylet 186B or the third stylet 186C can include a guidewire 188 extending distally therefrom, through the lumen 194 of the hub 192 and the second section 170.

In an embodiment, as shown in FIG. 2C, a distal portion of the stylet guidewire 188 can occlude a distal opening 196 to prevent a fluid from entering the lumen 194 as the second section 170 is advanced towards a target location within the vasculature 90. To note, the second guidewire 160 can extend through the first lumen 194A and can be configured to occlude the first opening 196A to, similarly, prevent a fluid from entering the first lumen 194A as the second section 170 is advanced towards a target location within the vasculature 90.

In an embodiment, one or more of the support stylets 186 can define a stylet lumen that is in fluid communication with a lumen of the flushing hub 106. A fluid can be introduced at the flushing hub 106 and pass through the manifold 182, through a lumen of the support stylet 186 and into a lumen 194 of the catheter 190 to flush the catheter 190 and purge the catheter 190 of any gases prior to placement.

With continued reference to FIGS. 1A-1C, in an embodiment, the catheter placement system 100 can include a needle 140, coupled to a needle retraction assembly 144 that is disposed within the interior cavity of the catheter housing 110. The needle 140 and needle retraction assembly 144 can be slidably engaged with the catheter housing 110 and can transition between an extended position (FIG. 1A) and a retracted position (FIG. 1B). The needle retraction assembly 144 can be coupled with a needle actuator 142 disposed on an outer surface of the catheter housing 110. Transitioning the needle actuator 142 between a distal position (FIG. 1A) and a proximal position (FIG. 1B) can transition the needle retraction assembly 144 and the needle 140 between the extended position and the retracted position. In use, a user can manipulate the needle actuator 142 and retract the needle 140 into the catheter housing 110. Advantageously, system 100 retains the needle 140 within the catheter housing 110 after use, mitigating accidental needle stick injuries or contamination from fluids, e.g. blood, disposed on the needle 140.

FIGS. 3A-3C show further details of the needle retraction assembly 144. The needle 140 can extend through the first side port 132A and can be disposed within the lumen of the first section 130. A proximal end of the needle 140 can be coupled to the needle retraction assembly 144 that is coupled with the needle retraction actuator 142. As shown in FIGS. 3A-3B, withdrawing the needle retraction actuator 142 proximally can withdraw the needle 140 proximally through the side port 132A, removing the needle 140 from the first lumen 194A.

In an embodiment, as shown in FIGS. 3A-3B and 4A-4B, the needle retraction actuator 142 can be slidably engaged with the needle retraction assembly 144 along the transverse axis. As such, as the needle 140 is withdrawn proximally, the needle 140 can displace transversely upward, away from the central axis of the first lumen 194A. Advantageously, the transverse movement of the needle 140 can allow for a clear pathway for additional elongate medical devices, e.g. the second guidewire 160, to be advanced through the first lumen 194A.

In an embodiment, as shown in FIGS. 3B-3C, the system 100 can further include a side port occluder 134 slidably engaged with the system 100 along a transverse axis and can be configured to close a side port 132, e.g. the first side port 132A, once the needle 140 is removed from the side port 132. The side port occluder 134 can be biased towards the closed position such that as soon as the needle 140 is fully removed from the side port 132, the side port occluder 134 transitions to the closed position (FIG. 3C). Advantageously, the side port occluder 134 can prevent any fluid from escaping from the first lumen 194A, when the needle 140 is removed.

With continued reference to FIGS. 1A-1C, the guidewire housing 120 can include one or more guidewire advancement assemblies. In an embodiment, the guidewire housing 120 can include a first guidewire 150 coupled to a first guidewire advancement assembly 154. The first guidewire 150 and first guidewire advancement assembly 154 can be slidably engaged with the guidewire housing 120. The first guidewire advancement assembly 154 can transition between a proximal position and a distal position. The first guidewire advancement assembly 154 can be coupled with a first guidewire actuator 152 disposed on an outer surface of the guidewire housing 120. Transitioning the first guidewire actuator 152 between the proximal position and the distal position can transition the first guidewire advancement assembly 154 and the first guidewire 150 between a retracted position and an extended position. In use, a user can manipulate the first guidewire actuator 152 to advance the first guidewire 150, into the vasculature 90, as described in more detail herein.

In an embodiment, the guidewire housing 120 can further include a second guidewire 160 coupled to a second guidewire advancement assembly 164 and slidably or rotatably engaged with the guidewire housing 120. The second guidewire advancement assembly 164 can transition the second guidewire 160 between a retracted position and an extended position. The second guidewire advancement assembly 164 can be coupled with a second guidewire actuator 162 disposed on an outer surface of the guidewire housing 120. In an embodiment, the second guidewire actuator 162 can be a scroll wheel, rotatably coupled with the guidewire housing 120. A portion of the scroll wheel can extend through a side wall of the guidewire housing 120. Rotating the second guidewire actuator 162 can extend or retract the second guidewire 160 along the longitudinal axis.

Figure 5:
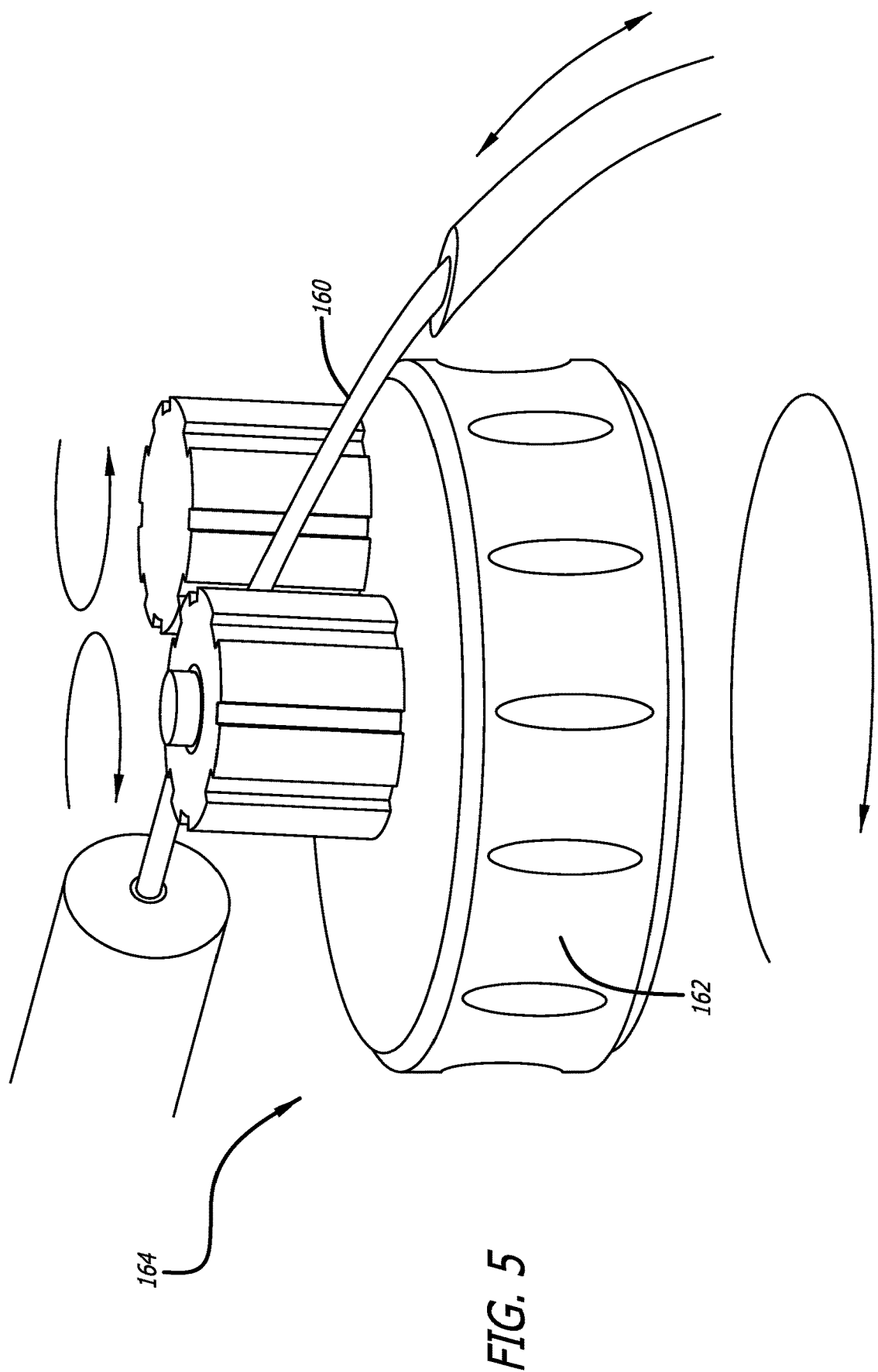
FIG. 5 illustrates a perspective view of a guidewire advancement assembly, in accordance with embodiments disclosed herein.

FIG. 5 shows further details of the scroll wheel actuator 162 of the second guidewire advancement assembly 164. The second guidewire actuator 162 can be coupled with one or more gears, wheels, or similar mechanisms configured to grasp, or compress the second guidewire 160 therebetween and to translate the rotational movement of the second guidewire actuator 162 into longitudinal movement of the guidewire 160.

With continued reference to FIGS. 1A-1C, in an embodiment, the catheter placement system 100 can further include a blood flash indicator 122. The blood flash indicator 122 can include a tube or similar structure formed from a transparent material and can be disposed within the guidewire housing 120. As noted, the guidewire housing 120 can be formed of a transparent material, as such a user can observe the blood flash indicator 122 disposed therein.

In an embodiment, the blood flash indicator 122 can define an interior cavity configured to maintain a vacuum therein. The blood flash indicator 122 can be in fluid communication with a lumen of the needle 140 by way of a communicating tube 124, or similar structure. As a distal tip of the needle 140 accesses a vasculature 90 of the patient, a fluid (e.g. blood) can flow proximally into the blood flash indicator 122 to be observed by a user. In an embodiment, a vacuum disposed within the blood flash indicator 122 can draw a fluid (e.g. blood) proximally through the needle lumen and into the blood flash indicator 122. A user can then observe a color or pulsatile flow characteristics to confirm vascular access. In an embodiment, the system 100 can include a blood flash actuator 126. Actuating the blood flash actuator 126 can open a valve or similar structure to place the vacuum disposed within the blood flash indicator 122, in fluid communication with the needle lumen to draw a fluid proximally therethrough. In an embodiment, the blood flash indicator 122 can further include a pump configured to be actuated by the user to create a vacuum within the blood flash indicator 122. For example, repeatedly actuating the blood flash actuator 126 can actuate the pump and create a vacuum within the blood flash indicator 122 to draw a fluid proximally through the needle lumen.

In an embodiment, the system 100 further includes a cap 108 configured to couple with a distal end of the catheter housing 110 and cover a distal portion of one of the needle 140 or the first section 130 of the catheter 190. The cap 108 can mitigate accidental needle stick injuries during storage or transport and maintains the needle 140, etc. in a sterile environment.

Figure 6A:
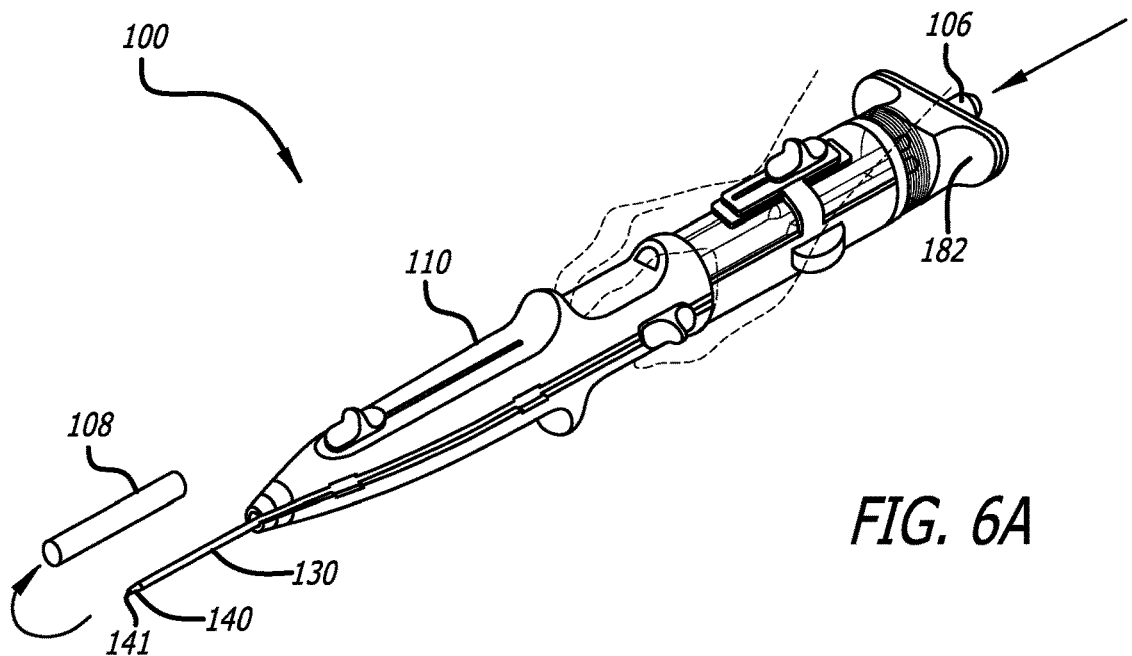
FIGS. 6A-6I illustrate steps in an exemplary method of use of a catheter placement system, in accordance with embodiments disclosed herein.

In an exemplary method of use, as shown in FIGS. 6A-6I, a catheter placement system 100 is provided, as described herein. Initially, as shown in FIG. 6A, a user can couple a syringe or medical fluid line to a flushing hub 106 disposed at a proximal end of catheter placement system 100. As shown, the flushing hub 106 extends from a proximal surface of the manifold 182. The manifold 182 provides fluid communication between the flushing hub 106 and one or more stylets 186, partially disposed within the extension legs of the extension set 180. Flushing fluid through the manifold 182, stylets 186 and into the lumen(s) 194 of the catheter 190 can purge the catheter 190 of any air, ready for placement within the vasculature 90. The catheter placement system cap 108 can be removed from the catheter housing 110.

Figure 6B:
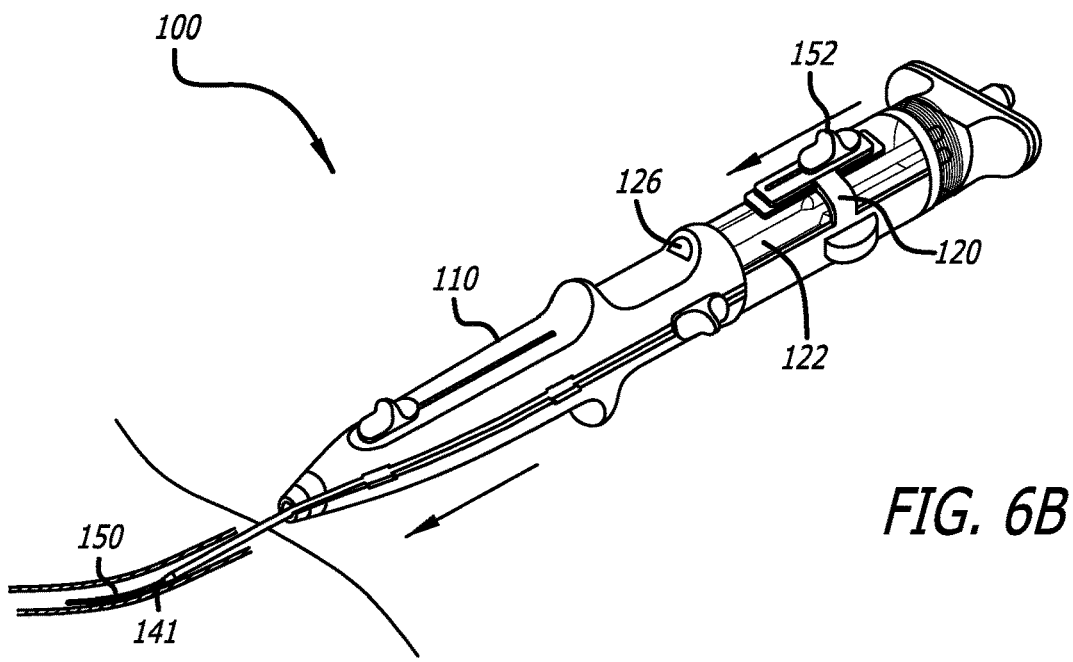

As shown in FIGS. 6A-6B, a user can grasp the catheter housing 110 and urge the needle tip 141 into a vasculature 90 of a patient. It is important to note that the catheter placement system 100 provides all of the components for placing the catheter 190, i.e. needle 140, blood flash indicator 122, catheter 190, first guidewire 150, second guidewire 160, stiffening system 184, etc. contained within a single sterile unit. This maintains all components that may be exposed to the patient within a sterile environment and contrasts with existing procedures that require repeated insertions using multiple components, risking the introduction of pathogens and the like. Further, the catheter placement system 100 maintains a barrier between the user and components that contact the patient, mitigating exposure to the patients' blood.

As shown in FIG. 6B, as the needle tip 141 accesses a vasculature 90 a blood flow can flow proximally through the needle lumen to a blood flash indicator 122. In an embodiment, the clinician can actuate a blood flash actuator 126 and provide fluid communication between a vacuum disposed within the blood flash indicator 122 and the needle lumen. Optionally, actuating or repeated actuating of the blood flash actuator 126 can form a vacuum within the blood flash indicator 122. The vacuum can draw the blood flow through the needle lumen and into the blood flash indicator 122. A user can then observe a color and pulsatile flow characteristics of the fluid disposed within the blood flash indicator 122 to confirm correct vascular access. For example a bright red color or strong pulsatile flow can indicate arterial access, a dark red color and low pulsatile flow can indicate venous access. Optionally, a user can compress the flexible blood flash indicator tube 122 to induce blood to flow therein. As shown, both the blood flash indicator 122 and a guidewire housing 120 in which the blood flash indicator 122 is disposed, can include a transparent material to allow a user to observe the blood flow therein.

In an embodiment, with correct vascular access confirmed, a user can actuate the first guidewire actuator 152 to advance the first guidewire 150 through the needle lumen and into the vasculature 90 of the patient until a distal tip of the first guidewire 150 extends distally of the needle tip 141, within the vasculature 90. In an embodiment, a distal tip of the first section 130 can be advanced into the vasculature along with the needle 140, as the needle accesses the vasculature. The distal tip of the first section 130 can be disposed on an outer surface of the needle 140 and can fit tightly therewith to prevent fluids, blood, or tissue from being urged between the needle 140 and first section 130 as the needle access the vasculature.

Figure 6C:
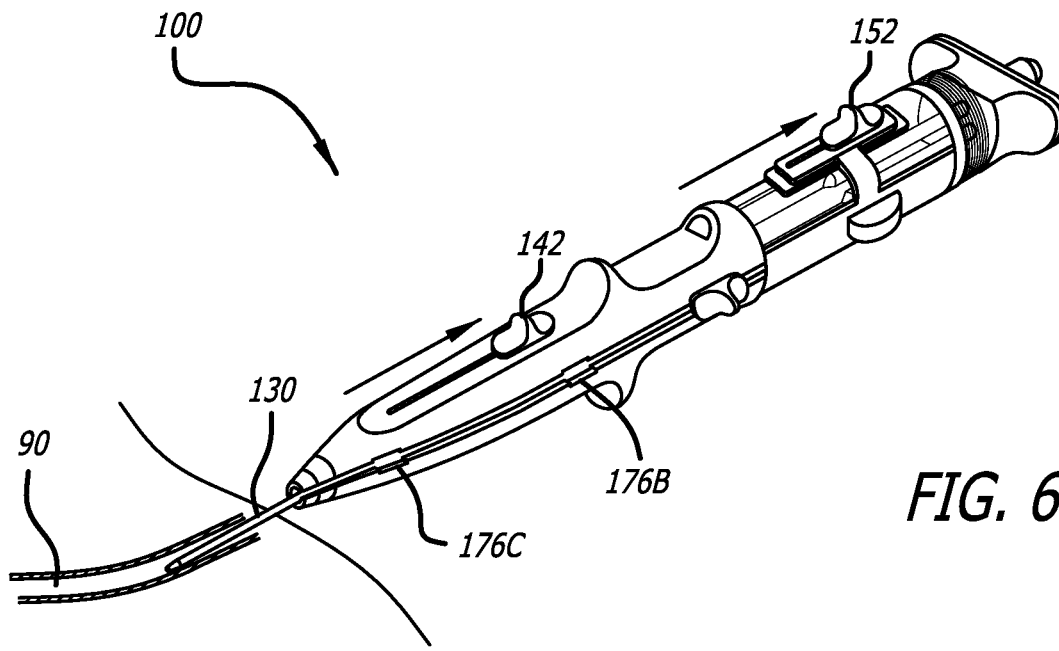

As shown in FIG. 6C, with the first section 130 of the catheter 190 disposed within the vasculature 90, the clinician can actuate a needle retraction actuator 142 to retract the needle 140 into the catheter housing 110. Advantageously, the needle 140 can be contained within the catheter housing 110 to mitigate accidental needle stick injuries and prevent contamination from fluids disposed thereon. In an embodiment, the clinician can actuate the first guidewire actuator 152 to retract the first guidewire 150 into the catheter housing 110. Advantageously, the first guidewire 150 can provide columnar support to the first section 130 as the needle 140 is retracted. In an embodiment, after the needle 140 is retracted, the catheter placement system 100 can be advanced distally to further advance the first section 130 into the vasculature 90. The first guidewire 150 can provide columnar support to the first section 130 as the system 100 is advanced distally. The first guidewire 150 can then be retracted once the first section 130 has been advanced into the vasculature. In an embodiment, the needle 140 and the first guidewire 150 can be retracted simultaneously.

Figure 6D:
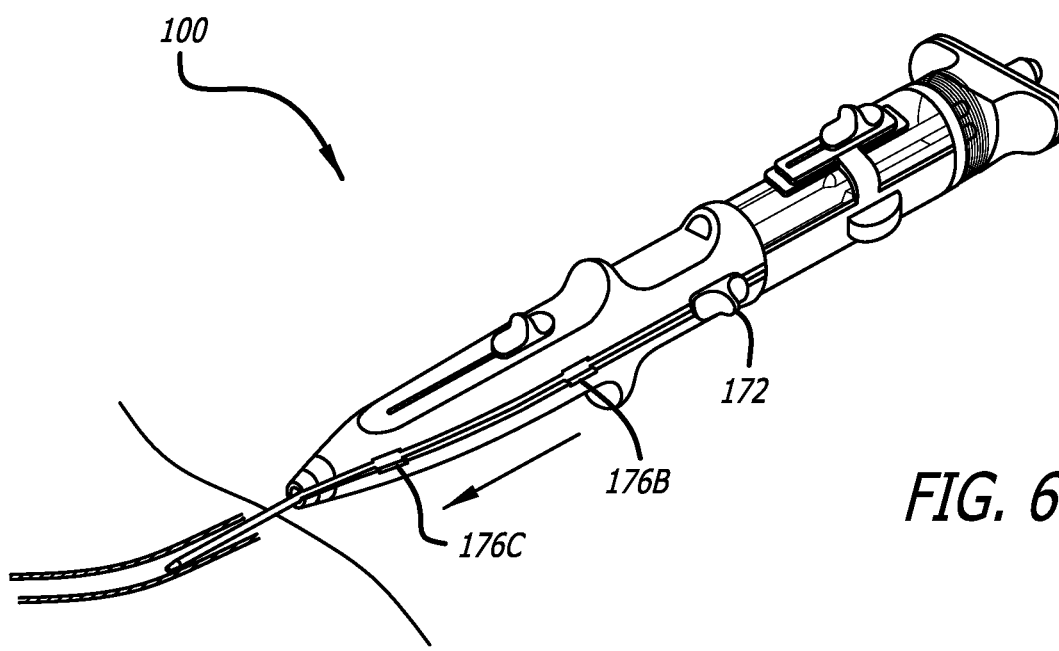

As shown in FIG. 6D, in an embodiment, the clinician can actuate a catheter actuator 172 from a first position to a second position to advance the first section 130 of the catheter 190 further into the vasculature 90. As shown, the catheter housing 110 can include a first notch 176A disposed at the first position, a second notch 176B disposed at the second position and a third notch 176C disposed at a third position. Each notch 176 can be configured to capture the catheter actuator 172 as the actuator 172 slides past the notch 176, to provide some resistance to further longitudinal movement. As such, the notches 176 can provide tactile feedback to the user to indicate when the catheter actuator 172 is disposed at one of the first, second, or third positions. As described herein, as the catheter 190 is advanced distally, the stiffening system 184 remains stationary relative to the housings 110, 120. As such the stiffening system is passively removed from the catheter 190 as the catheter 190 is advanced.

Figure 6E:
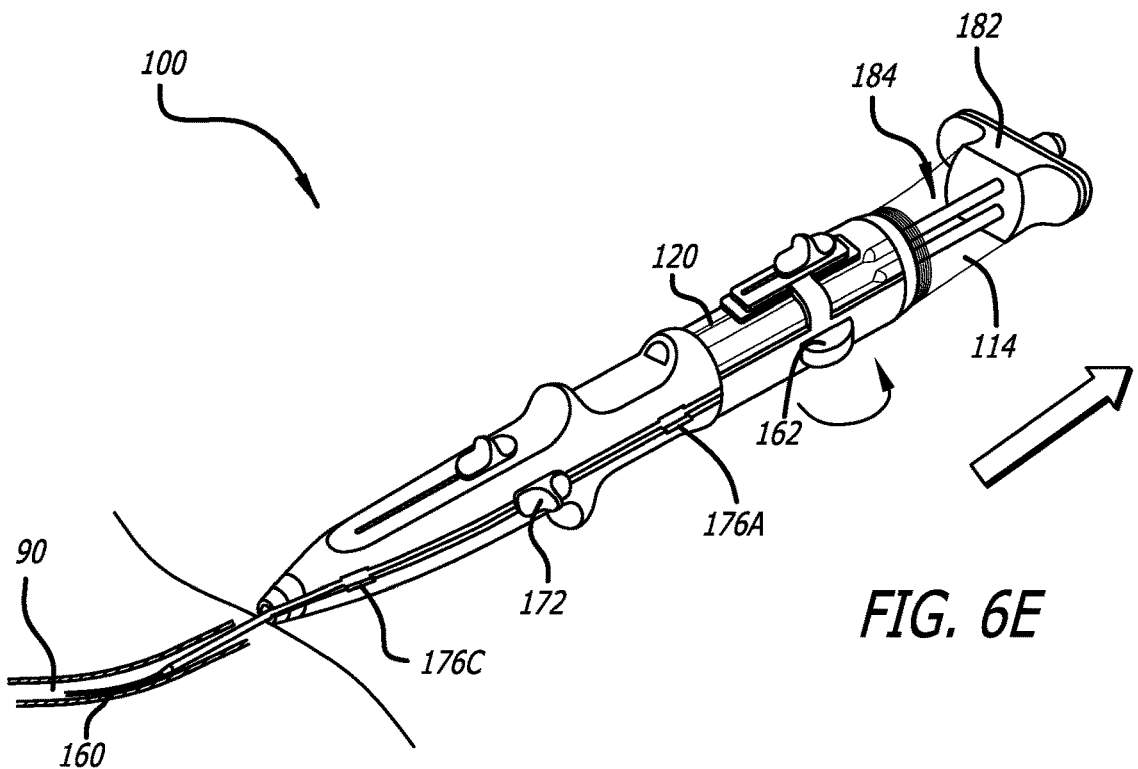

As shown in FIG. 6E, in an embodiment, the clinician can actuate the second guidewire actuator 162 to advance the second guidewire 160 through the first section 130 of the catheter 190 and into the vasculature 90. A distal tip of the second guidewire 160 can advance distally of a distal tip of the first section 130 to a target location within the vasculature 90. In an embodiment, the manifold 182 can be urged proximally to disengage from the proximal end of the guidewire housing 120 and withdraw the stiffening system 184 proximally. As noted, the collapsible film barrier 114 extending between the manifold 182 and the guidewire housing 120 can maintain the stiffening system 184 within a sterile environment, within the interior cavity of the catheter placement system 100.

Figure 6F:
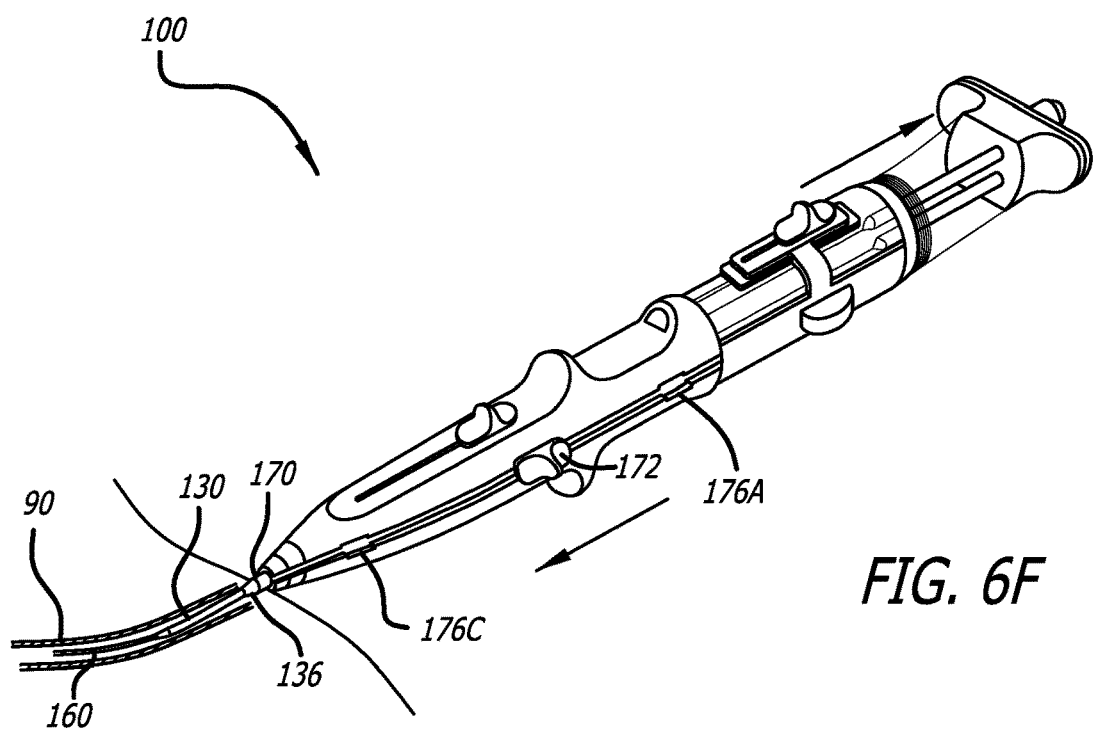

As shown in FIG. 6F, in an embodiment, the catheter actuator 172 can be advanced distally from the second position at the second notch 176B to the third position at the third notch 176C to advance the transition section 136 and the second section 170 into the vasculature 90. The transition section 136 can dilate the insertion site to allow the second section 170 to enter the vasculature 90.

Figure 6G:
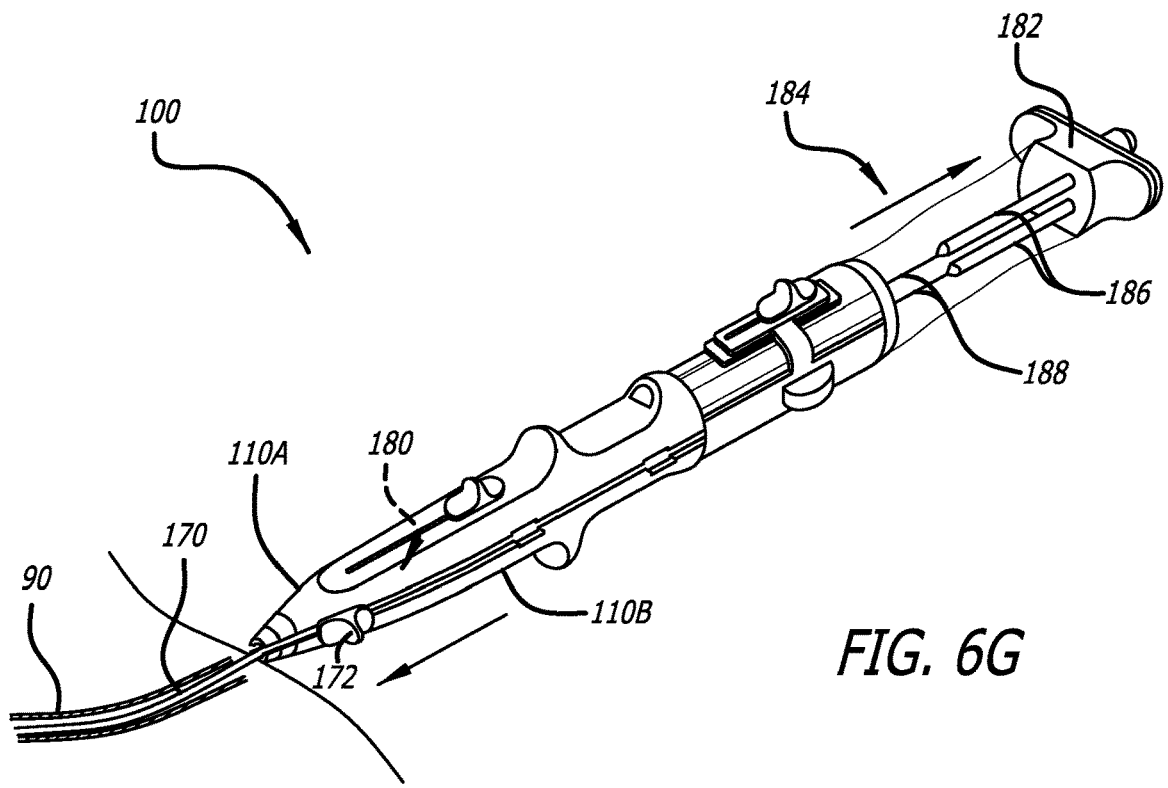

As shown in FIG. 6G, in an embodiment, with the catheter actuator 172 disposed in the third position, the catheter advancement assembly 174 engage a cam structure disposed on an interior surface of the catheter housing 110, and configured to separate the top catheter housing piece 110A from the bottom catheter housing piece 110B. Further, the manifold 182 can be fully withdrawn proximally to fully disengage the stiffening system 184 from the catheter 190.

Figure 6H:
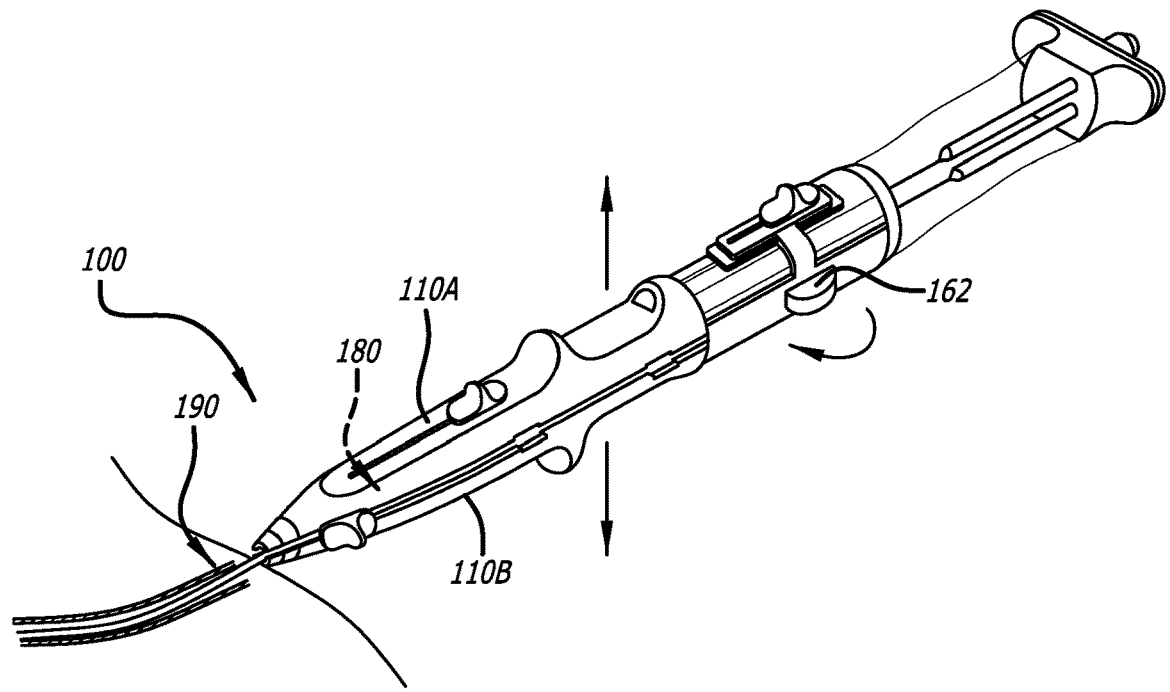

As shown in FIG. 6H, in an embodiment, the clinician can actuate the second guidewire actuator 162 to retract the second guidewire 160 from the catheter 190 and into the guidewire housing 120. Further, the top housing piece 110A and the bottom housing piece 110B can be further separated by the clinician to allow the hub 192 and extension set 180 to be removed from the catheter housing 110.

Figure 6I:
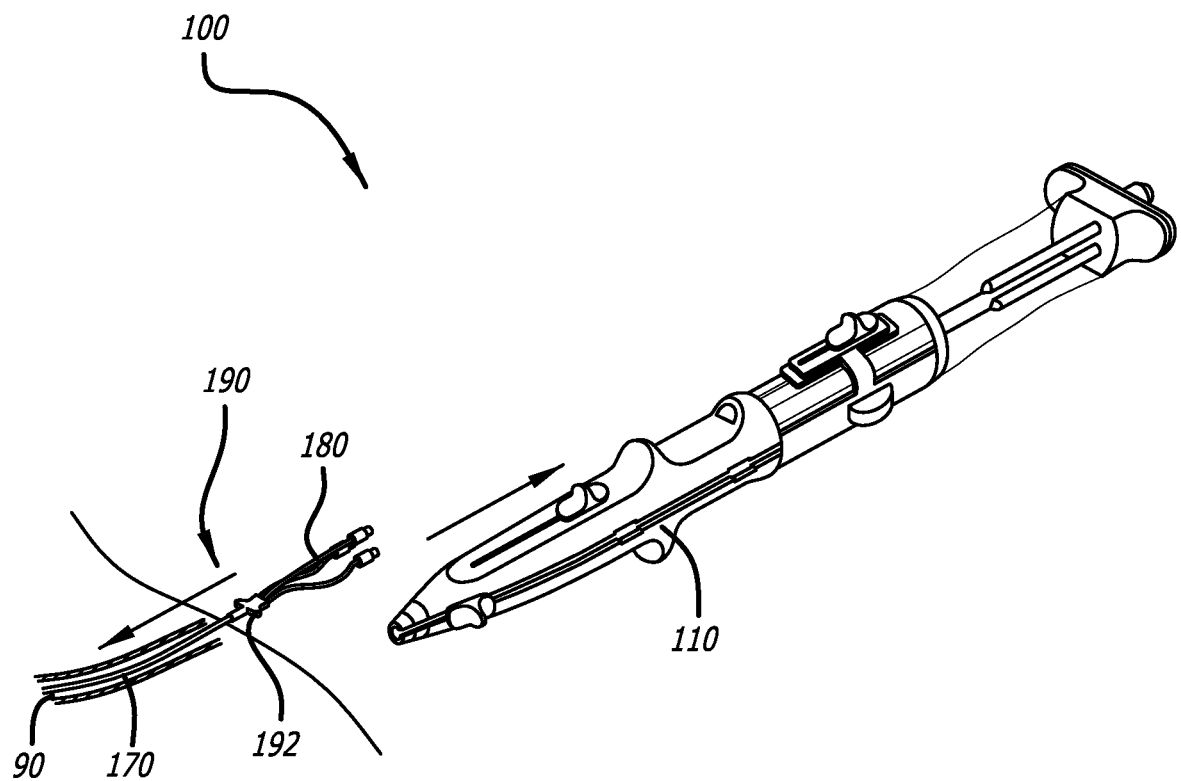

As shown in FIG. 6I, in an embodiment, with the catheter 190 placed at a target location within the vasculature 90, the catheter housing 110 can disengage the catheter 190 and the extension set 180. The catheter 190 can then be stabilized proximate the insertion site and a syringe or medical fluid line can be coupled to the extension set.

FIGS. 7A-7D show the movement of the inner components of the catheter placement system 100 with the outer housings removed for ease of explanation. In an embodiment, as shown in FIG. 7A, the needle tip 141 is advanced into the vasculature 90 to allow a blood flow to the blood flash indicator 122 by way of a communicating tube 124 providing fluid communication between the needle lumen and the blood flash indicator 122. FIG. 7B shows the first guidewire actuator 152 being advanced to advance the first guidewire 150 through the lumen of the needle 140 and into the vasculature 90. FIG. 7C shows the needle actuator 142 being withdrawn to withdraw the needle 140 from the lumen of the first section 130. FIG. 7D shows the first guidewire actuator 152 being withdrawn proximally to withdraw the first guidewire 150.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system, comprising:
   a housing defining an interior cavity and configured to maintain a sterile environment therein;
   a catheter comprising:
      a catheter tube having a first section, a second section, and a transition section disposed therebetween, one or both of the transition section and the second section disposed within the sterile environment defined by the housing;
      a hub supporting a proximal end of the second section;
      a first extension leg extending proximally from the hub and communicating with a first lumen of the catheter tube; and
      a second extension leg extending proximally from the hub and communicating with a second lumen of the catheter tube;
   a needle extending through a distal portion of the first lumen; and
   a stiffening system comprising:
      a first stylet comprising a first stylet lumen positioned in a proxmial portion of the first lumen; and
      a second stylet comprising a second stylet lumen and a stylet guidewire, a proximal end of the stylet guidewire coupled to a distal end of the second stylet, the second stylet positioned in a proximal portion of the second lumen, the stylet guidewire extending through the hub into the second section.

2. The catheter placement system according to claim 1, wherein the needle extends through a first side port of the catheter into a distal portion of the first lumen, a distal portion of the needle and a distal portion of the first section extending from a distal end of the housing.

3. The catheter placement system according to claim 2, further including a needle retraction assembly configured to withdraw the needle proximally from the first lumen and dispose the needle in an offset position from an axis of the first lumen within the interior cavity.

4. The catheter placement system according to claim 2, further including a first guidewire advancement assembly configured to advance a first guidewire through the first side port of the catheter and through a distal portion of the first lumen.

5. The catheter placement system according to claim 4, further including a second guidewire assembly including a scroll wheel actuator configured to rotate and advance a second guidewire through the first lumen.

6. The catheter placement system according to claim 1, wherein the stiffening system further includes a third stylet comprising a third stylet lumen and a second stylet guidewire, a proximal end of the second stylet guidewire coupled to a distal end of the third stylet, the third stylet positioned in a proximal portion of a third lumen of the catheter, the second stylet guidewire extending through the hub into the second section of the catheter.

7. The catheter placement system according to claim 6, wherein the second lumen communicates with a distal opening disposed in a sidewall of the second section, a distal portion of the stylet guidewire configured to selectively occlude the distal opening.

8. The catheter placement system according to claim 1, further including a catheter advancement assembly configured to advance the catheter distally, and configured to separate a top half of the housing from a bottom half of the housing when advanced to a distal position.

9. The catheter placement system according to claim 1, further including a manifold including a flushing hub in fluid communication with one or both of the first stylet lumen and the second stylet lumen, the manifold configured to support the stiffening system.

10. The catheter placement system according to claim 2, further including a blood flash indicator disposed within the interior cavity and in fluid communication with a lumen of the needle.

11. The catheter placement system according to claim 1, wherein the second stylet defines a more rigid mechanical characteristic relative to the stylet guidewire.

\* \* \* \* \*